United States Patent [19]
Beriger et al.

[11] 3,966,921
[45] June 29, 1976

[54] CERTAIN PESTICIDAL PHOSPHORUS CONTAINING AMIDINES

[75] Inventors: Ernst Beriger, Allschwil; Odd Kristiansen, Reinach; Kurt Rüfenacht, Basel, all of Switzerland; Jörg Bader, deceased, late of Arlesheim, Switzerland, by Dagmar Bader-Ludwig, legal representative

[73] Assignee: Ciba-Geigy Corporation, Ardsley, N.Y.

[22] Filed: May 5, 1975

[21] Appl. No.: 574,799

Related U.S. Application Data

[62] Division of Ser. No. 340,805, March 13, 1973, Pat. No. 3,882,103.

[30] Foreign Application Priority Data

Mar. 17, 1972 Switzerland.......................... 4054/72

[52] U.S. Cl................................ 424/211; 424/200; 424/210
[51] Int. Cl.².......................................... A01N 9/36
[58] Field of Search................... 424/220, 211, 200

[56] References Cited
UNITED STATES PATENTS

| 3,121,084 | 2/1964 | Winberg............................ 260/968 |
| 3,801,679 | 4/1974 | Hoffman et al..................... 424/220 |
| 3,880,958 | 4/1975 | Hoffman et al..................... 424/220 |

FOREIGN PATENTS OR APPLICATIONS

| 1,223,381 | 8/1966 | Germany............................ 260/945 |

*Primary Examiner*—V. D. Turner
*Attorney, Agent, or Firm*—Harry Falber

[57] ABSTRACT

Compounds of the formula

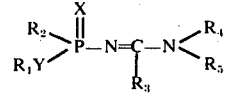

wherein
$R_1$ represents phenyl, or phenyl mono- to trisubstituted by halogen, mono- or disubstituted by $C_1$–$C_4$-alkyl, $C_1$–$C_4$-alkylthio, nitro, cyano or trifluoromethyl, or monosubstituted by $C_1$–$C_4$-carbalkoxy,
$R_2$ represents methyl, methoxy, ethyl, ethoxy or phenyl,
$R_3$ represents hydrogen or methyl,
$R_4$ and $R_5$ represent methyl, ethyl, n-propyl, isopropyl or allyl,
X and Y represent oxygen or sulphur, or
$R_4$ and $R_5$ with the nitrogen atom to which they are bound form the morpholino, piperidino or pyrrolidino ring, or
$R_3$ with $R_4$ or $R_5$ forms a 5- or 6-membered saturated ring, whereby then the group $R_4$ or $R_5$ not participating in the ring formation represents methyl or ethyl,
a process for their manufacture and their use for the control of pests, especially for the control of phytopathogenic nematodes, are disclosed.

11 Claims, No Drawings

CERTAIN PESTICIDAL PHOSPHORUS CONTAINING AMIDINES

This is a divisional of application Ser. No. 340,805 filed on Mar. 13, 1973 now U.S. Pat. No. 3,882,103.

The present invention relates to N-phosphoryl amidines, N-phosphorothioyl amidines, N-phosphonyl amidines and N-phosphonothioyl amidines, to processes for their production, and to their use for pest control.

The amidines correspond to the formula

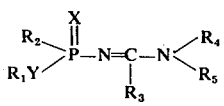

(I)

wherein $R_1$ represents phenyl, or phenyl mono- to trisubstituted by halogen, mono- or disubstituted by $C_1$–$C_4$-alkyl, $C_1$–$C_4$-alkylthio, nitro, cyano or trifluoromethyl, or monosubstituted by $C_1$–$C_4$-carbalkoxy, $R_2$ represents methyl, methoxy, ethyl, ethoxy or phenyl, $R_3$ represents hydrogen or methyl, $R_4$ and $R_5$ represent methyl, ethyl, n-propyl, isopropyl or allyl, X and Y represent oxygen or sulphur, or $R_4$ and $R_5$ with the nitrogen atom to which they are bound form the morpholino, piperidino or pyrrolidino ring, or $R_3$ with $R_4$ or $R_5$ forms a 5- or 6-membered saturated ring, whereby then the group $R_4$ or $R_5$ not participating in the ring formation represents methyl or ethyl.

The $C_1$–$C_4$-alkyl, $C_1$–$C_4$-alkylthio and $C_1$–$C_4$-carbalkoxy groups as substituents on the phenyl nucleus of the radical $R_1$ can be branched or straight-chain. Examples of such groups are: methyl, ethyl, isopropyl, n-propyl, n-, i-, sec.-, tert.-butyl, methylthio, ethylthio, n-propylthio, isopropylthio, n-butylthio, carbomethoxy, carbethoxy and isopropoxycarbonyl.

By halogen is meant fluorine, chlorine, bromine or iodine, particularly chlorine, bromine or iodine.

The compounds of formula I preferred on account of their action are those wherein $R_1$ represents the groups 3-methyl-4-methylthiophenyl, 4-nitrophenyl, 3-methyl-4-nitrophenyl, 2,5-dichloro-4-bromophenyl, 2,5-dichloro-4-iodophenyl, 4-methylphenyl, 2,4-dibromo-5-chlorophenyl, 2,4,5-trichlorophenyl, 3-chlorophenyl, 3-trifluoromethylphenyl, 4-methylthiophenyl, 4-chlorophenyl or 4-cyanophenyl, $R_2$ represents methyl, methoxy, ethyl or ethoxy, $R_3$ represents hydrogen, $R_4$ and $R_5$ represent methyl or ethyl, or $R_4$ and $R_5$ together with the nitrogen atom to which they are bound form the morpholino, piperidino or pyrrolidino ring, X represents sulphur, and Y represents oxygen.

Compounds of formula I forming a particularly preferred group are such compounds wherein $R_1$ represents the 3-methyl-4-methylthio group, $R_2$ represents methyl, methoxy, ethyl or ethoxy, $R_3$ represents hydrogen, $R_4$ and $R_5$ represent methyl or ethyl, X represents sulphur, and Y represents oxygen.

The compounds of formula I can be produced by the following methods known per se:

1) 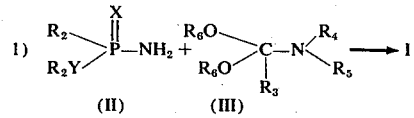

Reaction temperature −50°C to + 100°C

2) 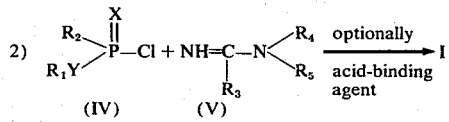

Reaction temperature −50°C to + 100°C

Conversion:

3) 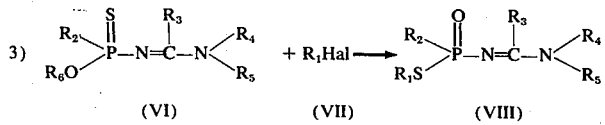

In formulae II to VIII, the symbols $R_1$ to $R_5$, X and Y have the meanings given for formula I, $R_6$ stands for $C_1$–$C_4$-alkyl, and Hal for chlorine, bromine, iodine or for the radical of a sulphuric acid ester.

Applicable acid-binding agents are: tertiary amines, e.g. trialkylamines, pyridine, pyridine bases or dialkylanilines; inorganic bases such as hydrides or hydroxides; carbonates and bicarbonates of alkali metals and alkaline-earth metals. The processes 1 and 2 are carried out at normal pressure, with the exclusion of moisture, and in inert solvents or diluents.

Suitable inert solvents or diluents are, for example: ethers and ethereal compounds such as diethyl ether, dipropyl ether, dioxane, tetrahydrofuran; aliphatic, aromatic as well as halogenated hydrocarbons, particularly benzene, toluene, xylenes, chloroform or chlorobenzene; and nitriles such as acetonitrile.

The starting materials of formulae II to V are in some cases known compounds (cp. e.g. DOS 2,019,597), or can be produced by methods analogous to known methods. Thus, the methods of production of the amide acetals required in the case of process I are described in 'Zeitschrift fur Chemie' 9, 201 (1969), and the production of (thio)phosphoric acid amides in Houben-Weyl, 'Methoden der organischen Chemie' (Methods of Organic Chemistry), Vol. Phosphorus II.

The active substances of formula I are suitable for the control of the most diverse animal pests. The said active substances can be used, for example, against all development stages, such as eggs, larvae, nymphs, pupae and adults of insects and members of the order acarina, such as mites and ticks.

They can be used, for example, against the following insects or members of the order acarina: Insects of the families: Tettigonidae, Gryllidae, Gryllotalpidae, Blattidae, Reduviidae, Phyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Galleridae, Culicidae, Tipulidae, Stomoxydae, Muscidae, Calliphoridae, Trypetidae and Pulicidae; as well as acarids of the families: Ixodidae, Tetranychidae and Dermanyssidae.

The insecticidal or acaricidal action can be substantially broadened and adapted to suit the given circumstances by the addition of other insecticides and/or acaricides. Suitable additives are, for example, the following active substances:

Organic Phosphorus Compounds

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4,5-trichlorophenylthiophosphate (RONNEL)
O-ethyl-O,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-iodophenyl)-thiophosphate (JODOFENPHOS)
4-tert.butyl-2-chlorophenyl-N-methyl-O-methylamidophosphate (CRUFOMATE)
O,O-dimethyl-O-(3-methyl-4-methylmercaptophenyl)-thiophosphate (FENTHION)
isopropylamino-O-ethyl-O-(4-methylmercapto-3-methylphenyl)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)-phosphate
2-chloro-1-(2,4-dichlorophenyl)vinyl-diethylphosphate (CHLORFENVINPHOS) 2-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-O-(3-chloro-4-methyl-2-oxo-2-H-1-benzopyran-7-yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)thiophosphate (DIAZINON)
O,O-diethyl-O-(2-quinoxalyl)thiophosphate
O,O-dimethyl-S-(4-oxo-1,2,3-benzotriazin-3(4H)-ylmethyl)-dithiophosphate (AZINPHOSMETHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2yl)methyl]-O,O-dimethyldithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2-(O,O-dimethyl-phosphoryl-thiomethyl)-5-methoxypyrone-4-3,4-dichlorobenzyl-triphenylphosphonium-chloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-dimethylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)

O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethyl-thiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
dimethyl-p-(methylthio)phenylphosphate
O,O-dimethyl-O-p-sulphamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
diethyl-S-2-(ethylsulphinyl)ethyl dithiophosphate (OXIDISULFOTON)
bis-O,O-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
O,O-dimethyl-O-(2,2-dichloro-1-methoxy-vinyl)phosphate
bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
diisopropylaminofluorophosphate (MIPAFOX)
O,O-dimethyl-S-(morpholinylcarbamoylmethyl)dithiophosphate (MORPHOTHION)
bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
O-phenyl-O-p-nitrophenyl-methanethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-($\beta$-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene(1,5)
O-methyl-O-(2-i-propoxycarbonyl-1methylvinyl)-ethylamidothiophosphate.

NITROPHENOLS AND DERIVATIVES 4,6-dinitro-6-methylphenol, sodium salt [Dinitrocresol]
dinitrobutylphenol-(2,2',2'')-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)

6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-4-oxocyclopent-2enyl(I)-(cis÷trans)-chrysanthemum-monocarboxylate ÷trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbamyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifen]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-yny-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2', 4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl-formamidine
1-n-butyl-2-(2'-methyl-4'-chlorophenyl-imino)-pyrolidine.

Urea

N-2-methyl-4-chlorophenyl-N', N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methyl-carbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methyl-carbamoyl)-oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (AFROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate (FORMETANATE) at its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithiolane-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate 3-isopropylphenyl-N-methyl-N-methylthiomethyl-carbamate
O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-N-acetal-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-proparglyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2[dipropargylamino]-phenyl-N-methylcarbamate
4-[dipropargylamino]-3-tolyl-N-methylcarbamate
4-[dipropargylamino]-3,5-xylyl-N-methylcarbamate
2-[ally-isopropylamino]-phenyl-N-methylcarbamate
3-[allyl-isopropylamino]-phenyl-N-methylcarbamate

CHLORINATED HYDROCARBONS

γ-hexachlorocyclohexane [GAMMEXANE; LINDAN; γ HCH]
1,2,4,5,6,7,8,8-octachloro-3α,4,7,7α'tetrahydro-4,7-methylene indane [CHLORDAN]
1,4,5,6,7,8,8-heptachloro, 3α, 4,7,7α-tetrahydro-4,7-methylene indane [HEPTACHLOR]
1,2,3,4,10,10-hexachloro-1,4,4α,5,8,8α-hexahydro-endo-1,4-exo5,8-dimethanonaphthalene [ALDRIN]
1,2,3,4,10,10-hexachloro-6,7-epoxy-1,4,4α,5,6,7,8,8α-octahydro-exo-1,4-endo-5,8-dimethanonaphthalene [DIELDRIN]
1,2,3,4,10,10-hexachloro-5,7-epoxy-1,4,4α,5,6,7,8,8α-octahydro-endo-endo-5,8-dimethanonaphthalene [ENDRIN].

In the forefront are the good nematocidal properties of the compounds of formula I. They can be used, for example, for the control of the following phytopathogenic nematodes: *Meloidogyne spp., Heterodera spp., Ditylenchus spp., Pratylenchus spp., Paratylenchus spp., Anguina spp., Helicotylenchus spp., Tylenchorhynchus spp., Rotylenchulus spp., Tylenchulus semipen etrans, Radipholus sililis, Belonolaimus spp., Trichodorus spp., Longidorus spp., Aphelenchoides spp., Xiphinema spp.* and *Rhadinaphelenchus spp..*

The compounds of formula I can be used on their own or together with suitable carriers and/or additives. Suitable carriers and additives may be solid or liquid, and correspond to the substances common in formulation practice, such as, e.g. natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays, or solutions, the formulation of these preparations being effected in a manner commonly known in practice. Also to be mentioned are cattle dips and spray races, in which aqueous preparations are used.

The agents according to the invention are produced in a manner known per se by the intimate mixing and-/or grinding of active substances of formula I with the suitable carriers, optionally with the addition of dispersing agents or solvents which are inert to the active substances. The active substances can be obtained and used in the following preparation forms:

solid preparations:
  dusts, scattering agents, granulates, coated granulates, impregnated granulates and homogeneous granulates;
liquid preparations:
  a. water dispersible active substance concentrates: wettable powders, pastes, emulsions;
  b. solutions.

The solid preparations (dusts, scattering agents) are produced by the mixing of the active substances with solid carriers. Suitable carriers are, e.g. kaolin, talcum, bolc, loess, chalk, limestone, ground limestone, attapulgite, dolomite, diatomaceous earth, precipitated silicic acid, alkaline-earth silicates, sodium and potassium aluminum silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be very easily prepared by a process in which an active substance of formula I is dissolved in an organic solvent, the thus obtained solution applied to a granulated mineral, e.g. attapulgite, $SiO_2$, granicalcium, bentonite, etc., and the organic solvent then evaporated off.

It is possible also to produce polymer granulates; in this case the active substances of formula I are mixed with polymerisable compounds (urea/formaldehyde; dicyandiamide/formaldehyde; melamine/formaldehyde, or others); polymerisation is then carefully carried out in a manner which leaves the active substances unaffected, and granulation performed actually during the gel forming process. It is more favourable, however, to impregnate finished porous polymer granules (urea/-formaldehyde, polyacrylonitrile, polyester and others), having a specific surface area and a favourable predeterminable adsorption/desorption ratio, with the active substances, e.g. in the form of their solutions (in a low-boiling solvent), and to then remove the solvent. Polymer granulates of this kind can be also sprayed in the form of microgranulates, having bulk weights of preferably 300 g/liter to 600 g/liter, with the aid of spray apparatus. Spraying can be carried out over extensive areas of useful plant crops by the use of aeoplanes.

Granulates can also be obtained by the compacting of the carrier material with the active substances and additives, and a subsequent reducing operation.

Moreover, it is possible to add to these mixtures additives stabilising the active substance and/or non-ionic, anion-active and cation-active substances which improve, e.g. the adhesiveness of the active substances on plants and parts of plants (adhesives and agglutinants), and/or ensure a better wettability (wetting agents) as well as dispersibility (dispersing agents).

The following substances are, for example, suitable: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, the alkali metal and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents.

The wettable powders and pastes are obtained by the mixing and grinding of the active substances with dispersing agents and pulverulent carriers, in suitable devices, until homogeneity is obtained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of napthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable anti-foam agents are, e.g. silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are e.g. alcohols, benzene, xylene, toluene, dimethylsulphoxide, and mineral oil fractions boiling in the range of 120° to 350°C. The solvents must be practically odourless, non-phytotoxic, and inert to the active substances.

Furthermore, the agents according to the invention can be used in the form of solutions. For this purpose, the active substance, or several active substances, of the general formula I is dissolved in suitable organic solvents, solvent mixtures, or water. As organic solvents it is possible to use aliphatic and aromatic hydrocarbons, their chlorinated derivatives, alkylnaphthalenes, mineral oils on their own or in admixture with each other.

The content of active substance in the above described agents is between 0.1 and 95%; it is to be mentioned in this connection that in the case of application of the agents from an aeroplane, or by means of some other suitable application devices, concentrations of up to 99.5% can be used, or even the pure active substance.

The active substances of formula I can be prepared, e.g. as follows:

Dusts

The following substances are used for the preparation of (a) a 5% dust, and (b) a 2% dust:

a.
5 parts of active substance
95 parts of talcum.

b.
2 parts of active substance
1 part of highly dispersed silicic acid
97 parts of talcum.

The active substances are mixed and ground with the carriers.

Granulate

The following substances are used to produce a 5 % granulate:

5 parts of active substance,
0.25 parts of epichlorhydrin,
0.25 parts of cetyl polyglycol ether,
3.50 parts of polyethylene glycol,
91 parts of kaolin (particle size 0.3 – 0.8 mm).

The active substance is mixed with epichlorhydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25%, and (d) a 10% wettable powder:

a.
40 parts of active substance,
5 parts of sodium lignin sulphonate,
1 part of sodium dibutyl-naphthalene sulphonate,
54 parts of silicic acid.

b.
25 parts of active substance,
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

c.
25 parts of active substance, 2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin.

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a.
10 parts of active substance,
3.4 parts of epoxidised vegetable oil,
13.4 parts of a combination emulsifier consisting of fatty alcohol polyglycol ether and alkylaryl-sulphonate calcium salt,
40 parts of dimethylformamide,
43.2 parts of xylene.

b.
25 parts of active substance,
2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to produce, by dilution with water, emulsions of any desired concentration.

Spray

The following constituents are used to prepare a 5% spray:

5 parts of active substance,
1 part of epichlorhydrin,
94 parts of ligroin (boiling limits 160°–190°C).

EXAMPLE 1 a.
N,N-dimethyl-N'-O-methyl-O-(3,6-dichloro-4-iodophenyl)-thionophosphoryl-formamidine An amount of 10 g of N,N-dimethylformamide-dimethylacetal is poured over 25 g of O-methyl-O-(3,6-dichloro-4-iodophenyl)-thiophosphoric acid amide, and the whole shaken until a clear solution is obtained. All volatile fractions are then distilled off at 50°C/1 Torr to leave 28.6 g of the compound of the formula

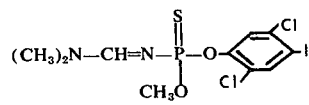

as viscous resin, which after a few days solidifies in crystalline form; M.P. 87° – 92°C.

b.
N-[O-(2,5-dichloro-4-iodophenyl)-O-methyl-thionophosphoryl]-piperidinyl-formimide 12.4 g of O-methyl-O-(3,6-dichloro-4-iodophenyl)-thiophosphoric acid amide is stirred with a mixture of 5.1 g of bis-methoxypiperidino-methane and 10 ml of dioxane for 10 minutes at 50°C; the starting material gradually dissolves and simultaneously the greater part of the reaction product precipitates in crystalline form. After cooling to 0°C, the product is filtered off and washed with methanol to obtain 12 g of the compound of the formula
M.P. 150° – 152°C.

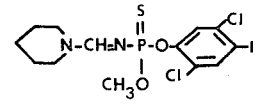

The following further compounds of formula I are produced in an analogous manner.

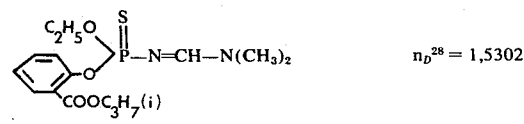  $n_D^{28} = 1{,}5302$

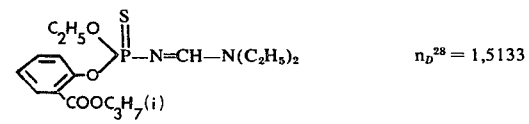  $n_D^{28} = 1{,}5133$

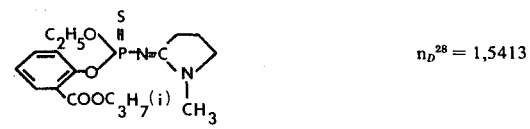  $n_D^{28} = 1{,}5413$

-continued
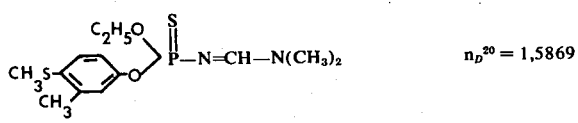     $n_D^{20} = 1.5869$
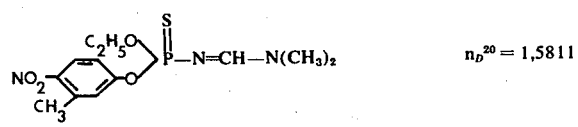     $n_D^{20} = 1.5811$
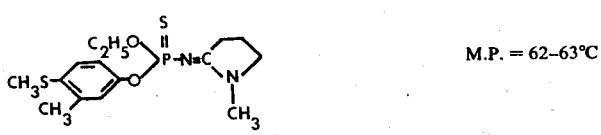     M.P. = 62–63°C
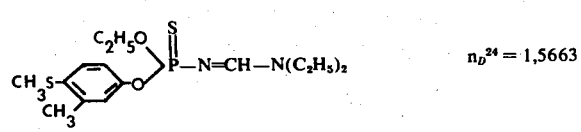     $n_D^{24} = 1.5663$
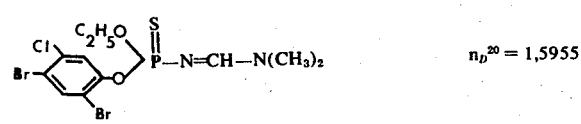     $n_D^{20} = 1.5955$
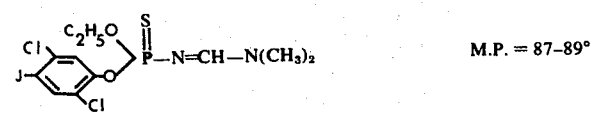     M.P. = 87–89°
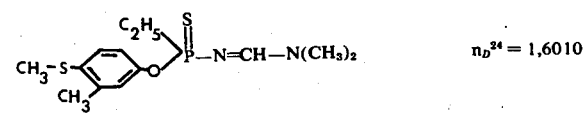     $n_D^{24} = 1.6010$
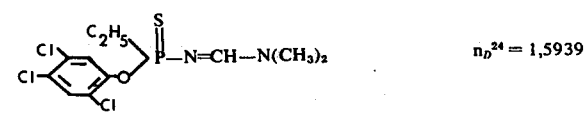     $n_D^{24} = 1.5939$
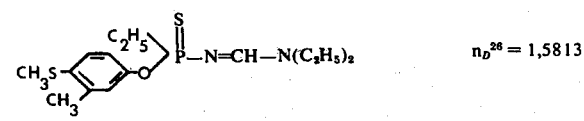     $n_D^{26} = 1.5813$
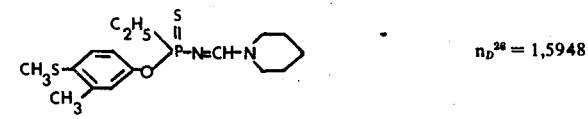     $n_D^{26} = 1.5948$
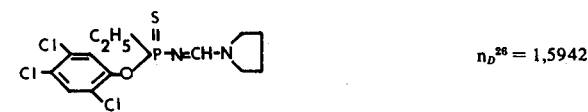     $n_D^{26} = 1.5942$ -continued
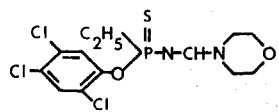 M.P. = 93–95°C
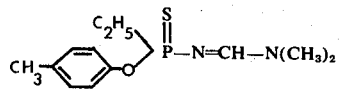 $n_D^{26} = 1{,}5631$
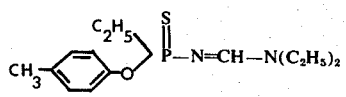 $n_D^{24} = 1{,}5523$
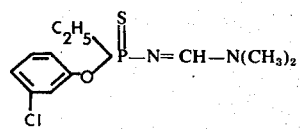 $n_D^{24} = 1{,}5810$
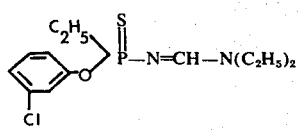 $n_D^{24} = 1{,}5615$
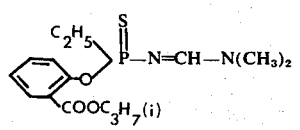 $n_D^{24} = 1{,}5448$
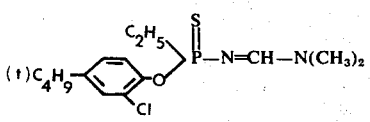 $n_D^{24} = 1{,}5492$
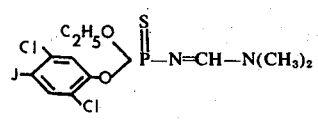 $n_D^{24} = 1{,}6343$
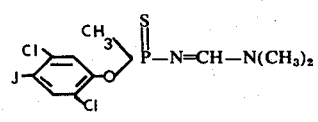 $n_D^{24} = 1{,}6423$
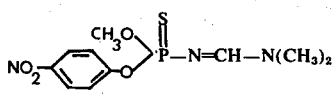 $n_D^{24} = 1{,}5836$
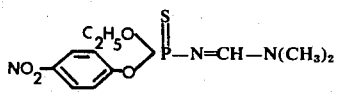 $n_D^{26} = 1{,}5740$
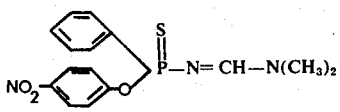 $n_D^{24} = 1{,}6155$ -continued
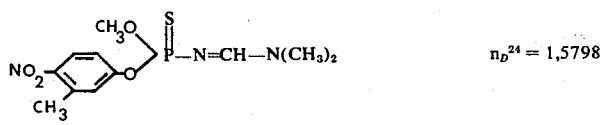           $n_D^{24} = 1{,}5798$
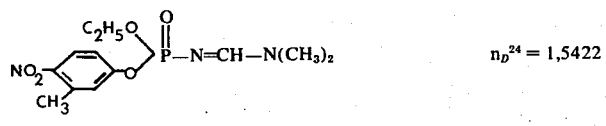           $n_D^{24} = 1{,}5422$
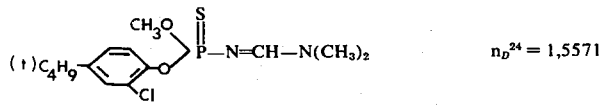           $n_D^{24} = 1{,}5571$
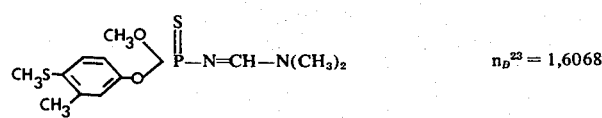           $n_D^{23} = 1{,}6068$
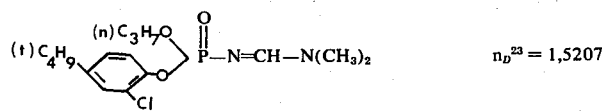           $n_D^{23} = 1{,}5207$
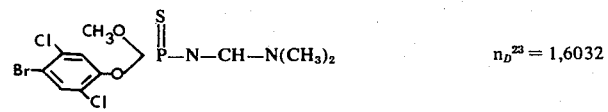           $n_D^{23} = 1{,}6032$
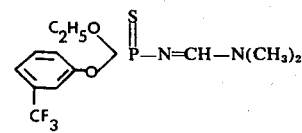
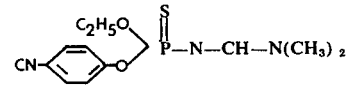
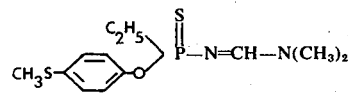
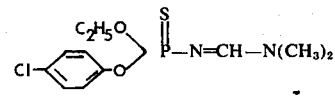
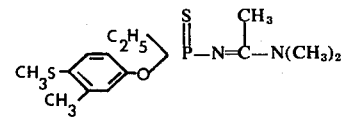
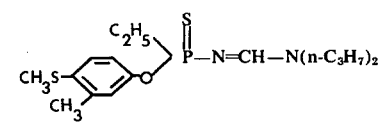

-continued

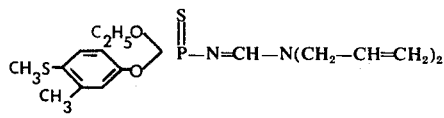

EXAMPLE 2

Insecticidal stomach poison action

Cotton and potato plants were sprayed with a 0.05% aqueous active-substance emulsion (obtained from a 10% emulsifiable concentrate). After the drying of the obtained coating, *Dysdercus fasciatus* nymphs were placed on the cotton plants, and Colorada beetle larvae (*Leptinotarsa decemlineata*) on the potato plants. The test was carried out at 24°C with 60% relative humidity.

The compounds according to Example 1 exhibited in the above test a good insecticidal stomach poison action against *Dysdercus fasciatus* and *Leptinotarsa decemlineata*.

EXAMPLE 3

Acaricidal action

A. Action against mites (*Tetranychus urticae*)

In order to test the acaricidal action, bean leaves infested by adults, dormant stages and eggs of the red spider mite (*Tetranychus urticae*) were treated with a 0.05% aqueous emulsion of the substance to be tested (prepared from a 25% emulsifiable concentrate). The test was evaluated after 6 days. The test insects were strains of the red spider mite resistant to esters of phosphoric acid.

B. Action against ticks and their development stages

1. *Rhipicephalus bursa* (adults and larvae)

In each case, 5 adult ticks or 50 tick larvae were placed into a small glass test tube, and the test tubes then immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool. An evaluation in the case of the adults was made after 2 weeks, and in the case of the larvae after 3 days. There were two repeats for each test.

2. *Boophilus micropulus* (females and larvae)

With a dilution series analogous to that in Test A, tests were carried out with 5 sensitive and OP-resistant females, respectively, or with 20 sensitive and OP-resistant larvae, respectively (resistance is with respect to diazinon compatibility). An evaluation in the case of the females was made after 6 weeks, and in the case of the larvae after 3 days.

The compounds according to Example 1 were effective in these tests against adults and larvae of *Rhipicephalus bursa* and against sensitive and OP-resistant females and larvae, respectively, of *Boophilus microplus*.

EXAMPLE 4

Action against soil nematodes

In order to test the action against soil nematodes the active substances were added, in the concentration stated in each case, to soil infested with root-gall-nematodes (*Meloidogyne arenaria*), and the whole intimately mixed. In the one test series, tomato seedlings were planted immediately afterwards in the thus prepared soil, and in the other test series tomatoes were planted after a waiting time of 8 days.

For an assessment of the nematicidal action, the galls present on the roots were counted 28 days after planting and sowing, respectively.

The active substances according to Example 1 exhibited in this test a good action against *Meloidogyne arenaria*.

It is claimed:

1. An insecticidal, acaricidal and nematocidal composition comprising an insecticidally, acaricidally and nematocidally effective amount of a compound of the formula

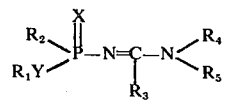

wherein
$R_1$ represents phenyl, or phenyl mono- to trisubstituted by halogen, mono- or disubstituted by $C_1$–$C_4$-alkyl, $C_1$–$C_4$-alkylthio, nitro, cyano or trifluoromethyl, or monosubstituted by $C_1$–$C_4$-carbalkoxy,
$R_2$ represents methyl, methoxy, ethyl, ethoxy or phenyl,
$R_3$ represents hydrogen or methyl,
$R_4$ and $R_5$ represent methyl, ethyl, n-propyl, isopropyl or allyl,
X and Y represent oxygen or sulphur, or
$R_4$ and $R_5$ with the nitrogen atom to which they are bound form the morpholino, piperidino or pyrrolidino ring, or
$R_3$ with $R_4$ or $R_5$ form a pyrrolidino or piperidino ring, whereby then the group $R_4$ or $R_5$ not participating in the ring formation represents methyl or ethyl,
together with a suitable inert carrier therefor.

2. The composition of claim 1, wherein in said compound, $R_1$ represents 3-methyl-4-methylthiophenyl, 4-nitrophenyl, 3-methyl-4-nitrophenyl, 2,5-dichloro-4-bromophenyl, 2,5-dichloro-4-iodophenyl, 4-methylphenyl, 2,4-dibromo-5-chlorophenyl, 2,4,5-trichlorophenyl, 3-chlorophenyl, 3-trifluoromethylphenyl, 4-methylthiophenyl, 4-chlorophenyl or 4-cyanophenyl; $R_2$ represents methyl, methoxy, ethyl or ethoxy; $R_3$ represents hydrogen; $R_4$ and $R_5$ represent methyl or ethyl, or $R_4$ and $R_5$ together with the nitrogen atom to which they are bound form the morpholino, piperidino or pyrrolidino ring; X represents sulphur; and Y represents oxygen.

3. The composition of claim 2, wherein in said compound, $R_1$ represents 3-methyl-4-methylthiophenyl; and $R_4$ and $R_5$ represent methyl or ethyl.

4. The composition of claim 3, wherein said compound is N,N-diethyl-N'-[O-(3-methyl-4-methylthiophenyl)-ethylthionophosphonyl]-formamidine.

5. The composition of claim 2, wherein said compound is N,N-diethyl-N'-[O-(4-methylthiophenyl)-ethyl-thionophosphonyl]-formamidine.

6. A method for combatting insects, acaricides and nematodes which comprises applying to the loci thereof an insecticidally, acaricidally and nematocidally effective amount of a compound of the formula

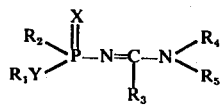

wherein
$R_1$ represents phenyl, or phenyl mono- to trisubstituted by halogen, mono- or disubstituted by $C_1$–$C_4$-alkyl, $C_1$–$C_4$-alkylthio, nitro, cyano or trifluoromethyl, or monosubstituted by $C_1$–$C_4$-carbalkoxy,
$R_2$ represents methyl, methoxy, ethyl, ethoxy or phenyl,
$R_3$ represents hydrogen or methyl,
$R_4$ and $R_5$ represent methyl, ethyl, n-propyl, isopropyl or allyl,
X and Y represent oxygen or sulphur, or
$R_4$ and $R_5$ with the nitrogen atom to which they are bound form the morpholino, piperidino or pyrrolidino ring, or
$R_3$ with $R_4$ or $R_5$ form a pyrrolidino or piperidino ring, whereby then the group $R_4$ or $R_5$ not participating in the ring formation represents methyl or ethyl.

7. The method of claim 6, wherein in said compound, $R_1$ represents 3-methyl-4-methylthiophenyl, 4-nitrophenyl, 3-methyl-4-nitrophenyl, 2,5-dichloro-4-bromophenyl, 2,5-dichloro-4-iodophenyl, 4-methylphenyl, 2,4-dibromo-5-chlorophenyl, 2,4,5-trichlorophenyl, 3-chlorophenyl, 3-trifluoromethylphenyl, 4-methylthiophenyl, 4-chlorophenyl or 4-cyanophenyl; $R_2$ represents methyl, methoxy, ethyl or ethoxy; $R_3$ represents hydrogen; $R_4$ and $R_5$ represent methyl or ethyl, or $R_4$ and $R_5$ together with the nitrogen atom to which they are bound form the morpholino, piperidino or pyrrolidino ring; X represents sulphur; and Y represents oxygen.

8. The method of claim 7, wherein in said compound, $R_1$ represents 3-methyl-4-methylthiophenyl; and $R_4$ and $R_5$ represent methyl or ethyl.

9. The method of claim 8, wherein said compound is N,N-diethyl-N'-[O-(3-methyl-4-methylthiophenyl)-ethyl-thionophosphonyl]-formamidine.

10. The method of claim 7, wherein said compound is N,N-diethyl-N'-[O(4-methylthiophenyl)-ethyl-thionophosphonyl]-formamidine.

11. The method of claim 6 for combatting phytopathogenic nematodes.

* * * * *